(12) United States Patent
Vinski et al.

(10) Patent No.: US 6,551,603 B1
(45) Date of Patent: Apr. 22, 2003

(54) COSMETIC SALT SCRUB PRODUCT

(75) Inventors: Paul Vinski, Danbury, CT (US); Craig Stephen Slavtcheff, Guilford, CT (US); Joanna Hong Zhang, Milford, CT (US); Brian Andrew Crotty, Branford, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 67 days.

(21) Appl. No.: 09/713,468

(22) Filed: Nov. 15, 2000

Related U.S. Application Data
(60) Provisional application No. 60/202,951, filed on May 9, 2000.

(51) Int. Cl.$^7$ .............................. A61K 6/00; A61K 7/00; A01N 25/00
(52) U.S. Cl. ........................ 424/401; 514/846; 514/844
(58) Field of Search ......................... 424/401; 514/846, 514/844

(56) References Cited

U.S. PATENT DOCUMENTS

| | | | | |
|---|---|---|---|---|
| 4,666,707 A | * | 5/1987 | Eguchi et al. ................. | 424/44 |
| 5,602,178 A | * | 2/1997 | Caroselli et al. ............. | 514/529 |
| 5,866,145 A | | 2/1999 | Stavroff et al. | |
| 5,955,057 A | * | 9/1999 | Maunder et al. .............. | 424/43 |
| 5,958,462 A | * | 9/1999 | McLean ..................... | 424/630 |

OTHER PUBLICATIONS

Biore Heat Mask—1998.
"Scrub Cosmetics"—1986.

* cited by examiner

*Primary Examiner*—Thurman K. Page
*Assistant Examiner*—Todd D Ware
(74) *Attorney, Agent, or Firm*—Milton L. Honig

(57) ABSTRACT

A cosmetic sea salt scrub is provided which includes sodium sesquicarbonate and an oil. Sodium sesquicarbonate ordinarily is the major salt present and amounts of this salt relative to the oil may range from about 20:1 to about 5:1 by weight. Mineral oil is particularly preferred as the oil phase. Salt scrubs according to this invention are relatively uniform in composition, easily dispensed from a jar and spread uniformly on the skin.

10 Claims, No Drawings

COSMETIC SALT SCRUB PRODUCT

This application claims benefit of priority to Provisional application Serial No. 60/202,951, filed May 9, 2000.

BACKGROUND OF THE INVENTION

1. Field of the Invention

The invention concerns a cosmetic salt scrub product of improved aesthetics and useful for exfoliation of skin surfaces.

2. The Related Art

Salt scrub products currently on the market typically consist of coarse salt grains immersed in a pool of oil. Visually observable is the phase separation between solid/salt phase and liquid/oil phase. The former sinks to the bottom of the container and the latter rises above the salt crystals. In most instances, the salt is sodium chloride known as rock salt.

Bath & Body Works, Inc. in U.S. Pat. 5,866,145 (Stavroff et al.) describe a body polisher product containing from about 50 to about 80% salt, from about 20 to 50% emollient and 0.1 to 2% fragrance. These ingredients are embodied as Dead Sea salt (sodium chloride), dimethicone and an unidentified perfume. Sea salt scrub products sold by Bath & Body Works and apparently related to the patent disclosure exhibit substantial phase separation. A pool of liquids float over a bed of solid rock in an aesthetically and functionally displeasing arrangement.

Accordingly, it is an object of the present invention to provide a cosmetic salt scrub composition which does not exhibit any gross separation of liquid and solid components.

Another object of the present invention is to provide a cosmetic salt scrub composition of visual uniformity and readily scoopable as a uniform mixture to apply to the skin.

These and other objects of the present invention will become more readily apparent from consideration of the following summary and detailed description.

SUMMARY OF THE INVENTION

A cosmetic salt scrub composition is provided which includes:

(i) from about 20 to about 95% by weight of sodium sesquicarbonate; and (ii) from about 2 to about 20% by weight of an oil.

DETAILED DESCRIPTION OF THE INVENTION

Now it has been found that replacement of traditional sea salt (sodium chloride) with sodium sesquicarbonate in admixture with oil achieves several benefits. Separation is avoided, dispensability from the container is easy and dispersibility onto the skin is highly uniform. Unlike sea salt, sodium sesquicarbonate does not float in the oily liquid phase. With sesquicarbonate much of the oil is absorbed onto the salt and albeit not powdery is relatively dry in feel.

Salts other than sodium sesquicarbonate may be included in compositions of the present invention. These salts may be sodium tripolyphospate, sodium aluminosilicate, silica, alumina, clays, talc, calcium carbonate, calcium sulphate, magnesium chloride and combinations thereof. Notwithstanding these other salts, sodium sesquicarbonate will be present at levels higher than any of the other salts. Sodium sesquicarbonate may range in concentration from about 20 to about 95%, preferably from about 50 to about 85%, optimally from about 60 to about 80% by weight. Other salts when present will ordinarily in total be no higher than about 15%, more preferably no higher than from about 0.001 to about 10%, optimally no higher than from about 0.01 to 5% by weight.

Oils are a second important element of the present invention. These oils may be selected from natural and synthetic oils. The natural oils may be of petroleum or vegetable origin. Petroleum oils include mineral oil, petrolatum, isoparaffins and mixtures thereof. Vegetable or animal derived oils may include sunflower seed oil, cottonseed oil, rapeseed oil, olive oil, cod liver oil, lanolin, castor oil, soybean oil, palm oil, coconut oil and combinations thereof. Synthetic oils may include esters, silicones, polyols, fatty alcohols and hydrocarbons. The esters include:

(1) Alkenyl or alkyl esters of aromatic carboxylates such as benzoic acid or of fatty acids having 10 to 20 carbon atoms. Examples thereof include isoarachidyl neopentanoate, isononyl isonanonoate, oleyl myristate, oleyl stearate, and oleyl oleate. Particularly preferred are $C_{12}$–$C_{15}$ alkyl benzoates available as Finsolv® TN and isostearyl palmitate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono- stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterol esters, of which cholesterol fatty acid esters are examples thereof.

Silicone oils may also be suitable for the present invention. These oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Polyhydric alcohols also known as polyols may be useful as oils. Representative polyols include glycerine, diglycerine, propylene glycol, dipropylene glycol, polypropylene glycol, polyethylene glycol and derivatives thereof, sorbitol, hydroxypropyl sorbitol, hexylene glycol, 1,2-butylene glycol, 1,2,6-hexanetriol, isoprene glycol, 2-methyl-1,3-propanediol, ethoxylated glycerol, propoxylated glycerol and mixtures thereof.

Fatty alcohols having from 8 to 30 carbon atoms may also be useful as oils for compositions of this invention. Representative fatty alcohols include lauryl, myristyl, palmityl, stearyl, isostearyl, hydroxystearyl, oleyl, linoleyl, ricinoleyl, behenyl and erucyl alcohols or combinations thereof.

Hydrocarbons suitable as oils for the present invention include polyolefins such as polydecenes and polybutenes. Particularly preferred are hydrocarbons sold under the Permethyl® 99 and 101 trademarks.

Amounts of the oil may range from about 2 to about 20%, preferably from about 5 to about 15%, optimally from about 8 to about 12% by weight.

Advantageously, the amount of sodium sesquicarbonate to oil may range from about 20:1 to about 5:1, preferably from about 15:1 to about 5:1, optimally from about 8:1 to about 6:1 by weight.

Although not essential, it is useful to formulate a water-soluble polymer mixed within the oil phase. Illustrative substances are polydimethylsiloxane-PEG, dimethicone copolyol phosphate (commercially available as Pecosil®), dimethicone sulfosuccinates, glyceryl polymethyacrylate and a variety of polyalkoxylated silicates. Amounts of the polymer may range from about 0.05 to about 10%, preferably from about 0.3 to about 5%, optimally from about 0.5 to about 2% by weight.

Thickeners may also be incorporated into the compositions. These include polyacrylamides, polyacrylates, cross-linked polyacrylates such as Carbomers, xanthan, carrageenan, pectin, guar gum, sodium carboxymethyl cellulose, hydroxymethyl cellulose, hydroxypropyl cellulose, ethyl cellulose, hydroxypropyl methylcellulose, polyoxyethylene-polyoxypropylene block copolymers and mixtures thereof.

A variety of skin conditioning and protective agents may be formulated with the cosmetic compositions. These agents may include preservatives, herbal extracts, vitamins, anti-irritant agents, emulsifiers and keratolytic agents.

Preservatives can desirably be incorporated into the compositions to protect against the growth of potentially harmful microorganisms. Suitable preservatives include alkyl esters of para-hydroxybenzoic acid, hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. Preservatives are preferably employed in amounts ranging from about 0.01% to about 2% by weight of the composition.

Herbal extracts may include Roman Chamomile, Green Tea, Scullcap, Nettle Root, Swertia Japonica, Fennel, Anise, Arnica, Calandula, Coltsfoot, Cornflower, Elder, Gentian, Hawthorn, Lavender, Linden, Myrrh, Oat, Rose, Sweet Clover, Sandalwood, Vetiver, Tulsi Kamala, Eucalyptus, St. John's Wort and Aloe Vera extracts. Amount of each of the extract may range from about 0.00001 to about 1%, preferably from about 0.01 to about 0.5%, optimally from about 0.05 to about 0.2% by weight of the composition.

Small beads of wax impregnated with a dye or pigment may be included in the compositions. Useful waxes include micro-crystalline polyethylene waxes, carnauba wax, candillia wax, beeswax and pistachio wax. Most preferred is the pistachio wax. Amounts of the waxes may range from about 0.01 to about 5%, preferably from about 0.1 to about 3%, optimally from about 0.5 to about 1.2% by weight.

Various colorants of the dye or pigment variety may be included in the compositions, especially within the wax spheres. Typical colorants include manganese dioxide, FD&C Blue 1, FD&C Yellow 10, FD&C Red 6, aluminum lakes, iron oxides, bismuth chloride, chromium oxides and combinations thereof. Amounts of the colorant may range from about 0.0001 to about 1%, preferably from about 0.01 to about 0.5%, optimally from about 0.1 to about 0.3% by weight.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLES 1–8

Several formulations of salt scrub products are listed within Table I below.

TABLE I

| IN-GREDIENTS | EXAMPLES | | | | | | | |
|---|---|---|---|---|---|---|---|---|
| | 1 | 2 | 3 | 4 | 5 | 6 | 7 | 8 |
| PHASE A | | | | | | | | |
| $C_{12}$–$C_{15}$ Alkyl Benzoate | 6.00 | 4.00 | 6.00 | 4.00 | 10.00 | 2.00 | 4.00 | 10.00 |
| Isostearyl Palmitate | 5.00 | 3.00 | 5.00 | 3.00 | 9.00 | 1.00 | 6.00 | 3.00 |
| Butylated Hydroxytoluene | 0.05 | 0.05 | 0.05 | 0.05 | 0.05 | 0.05 | 0.05 | 0.05 |
| PHASE B | | | | | | | | |
| Colorant | 0.06 | 0.06 | 0.06 | 0.06 | 0.06 | 0.06 | 0.06 | 0.06 |
| Sunflower Seed Oil | 3.00 | 1.00 | 2.00 | 1.00 | 1.00 | 1.00 | 1.00 | 1.00 |
| Mineral Oil | 11.90 | 8.90 | 8.90 | 2.90 | 10.90 | 8.90 | 5.90 | 2.90 |
| Polydimethylsiloxane-PEG | 1.00 | 1.00 | 1.00 | 1.00 | 1.00 | 1.00 | 1.00 | 1.00 |
| PHASE C | | | | | | | | |
| Fragrance | 1.25 | 1.25 | 1.25 | 1.25 | 1.25 | 1.25 | 1.25 | 1.25 |
| PHASE D | | | | | | | | |
| Sodium Sesquicarbonate | 70.73 | 79.73 | 74.73 | 85.73 | 65.73 | 83.73 | 79.73 | 79.73 |
| Pistachio Wax Spheres (Impregnated with Colorant) | 1.00 | 1.00 | 1.00 | 1.00 | 1.00 | 1.00 | 1.00 | 1.00 |
| Sea Salts | 0.01 | 0.01 | 0.01 | 0.01 | 0.01 | 0.01 | 0.01 | 0.01 |

Formulations in each of the examples may be prepared by combining the alkyl benzoates with isostearyl palmitate in a vessel under agitation forming a Phase A. Butylated hydroxytoluene is sprinkled slowly into the Phase A vessel and mixed until the combination is solubilized. Phase D ingredients are then blended together for thirty minutes. Phase B is premixed and then added to Phase A to form a homogeneous composition. Phase C is added to Phase A, B and the combination mixed until homogeneous. Thereafter Phase A, B, C are mixed with Phase D and blended until uniform.

EXAMPLE 9

Experiments were conducted to evaluate the effect of product aesthetics on the weight ratio of sodium sesquicarbonate to oil. Table II lists the components in the oil and the salt portions. More than 98% of the salt portion is sodium sesquicarbonate.

TABLE II

| INGREDIENT | WEIGHT % |
|---|---|
| OILS | |
| $C_{12}$—$C_{15}$ Alkyl Benzoate | 22.22 |
| Stearyl Palmitate | 16.67 |
| Sunflower Seed Oil | 5.56 |
| Mineral Oil (70 sus) | 50.00 |
| Polydimethylsiloxane-PEG (Polyderm Ppi-Si WS) | 5.55 |
| SALT | |
| Sodium Sesquicarbonate | 98.80 |
| Lapiz Blue Pistachio Wax spheres 20/40 | 1.19 |
| Sea Salts | 0.01 |

TABLE III

Physical Aesthetic Properties

| COMPOSITION (SALT/OIL BY WEIGHT) | INITIAL OBSERVATIONS | OVERNIGHT OBSERVATIONS | OBSERVATIONS AFTER TWO NIGHTS |
|---|---|---|---|
| 95:5 | Product too dry | Product too dry | Product too dry |
| 90:10 | Product too dry | Product too dry | Product too dry |
| 85:15 | Acceptable | Acceptable | Acceptable |
| 75:25 | Acceptable | Small oil pool on surface but acceptable | Small oil pool on surface but acceptable |
| 70:30 | Unacceptable: too much oil, product too wet | Unacceptable: large pool of oil on the surface | Unacceptable: large pool of oil on the surface |
| 65:35 | Unacceptable: too much oil, product too wet | Unacceptable: large pool of oil on the surface | Unacceptable: large pool of oil on the surface |

Salt and oil were blended together in a series of different ratios ranging from 95:5 down to 65:35. Ratios ranging from 95:1 to 75:25 provided an aesthetically acceptable product without any significant exudation of oil from the sesquicarbonate. Around ratios of 70:30 and lower, the product became aesthetically unacceptable.

Salts other than sodium sesquicarbonate were evaluated including tetrasodium pyrophosphate and sodium chloride. Phase separation between oil and salt was noted at relative weight ratios which produced acceptable aesthetics in the sesquicarbonate system.

The foregoing description and examples illustrate selected embodiments of the present invention. In light thereof variations and modifications will be suggested to one skilled in the art, all of which are within the spirit and purview of this invention.

What is claimed is:

1. A cosmetic salt scrub composition comprising:

(i) from about 20 to about 95% by weight of sodium sesquicarbonate; and (ii) from about 2 to about 20% by weight of an oil; the sesquicarbonate and oil being present in a weight ratio ranging from about 85:15 to about 75:25.

2. The composition according to claim 1 wherein sodium sesquicarbonate is present in an amount from about 50 to about 85% by weight.

3. The composition according to claim 1 wherein a sodium sesquicarbonate is present in an amount greater than any other salt.

4. The composition according to claim 1 wherein the weight ratio of sodium sesquicarbonate and oil ranges from about 20:1 to about 5:1.

5. The composition according to claim 1 further comprising from about 0.05 to about 10% by weight of a water soluble polymer.

6. The composition according to claim 5 wherein the water-soluble polymer is polydimethylsiloxane-PEG.

7. The composition according to claim 1 further comprising from about 0.01 to about 5% by weight of colored wax spheres.

8. The composition according to claim 1 further comprising salts other than sodium sesquicarbonate, the other salts when present in total being in an amount no higher than about 15% by weight of the composition.

9. The composition according to claim 8 wherein the other salts range in amount from about 0.01 to about 5% by weight of the composition.

10. The composition according to claim 1 wherein sodium sesquicarbonate is present in an amount from about 60 to about 80% by weight of the composition.

\* \* \* \* \*